US009592284B2

(12) United States Patent
Wilson et al.

(10) Patent No.: US 9,592,284 B2
(45) Date of Patent: Mar. 14, 2017

(54) IMMUNIZATION REGIMEN WITH E4-DELETED ADENOVIRUS PRIME AND E1-DELETED ADENOVIRUS BOOST

(75) Inventors: James M. Wilson, Glen Mills, PA (US); Yan Zhi, Malvern, PA (US)

(73) Assignee: The Trustees of the University of Pennsylvania, Philadelphia, PA (US)

( * ) Notice: Subject to any disclaimer, the term of this patent is extended or adjusted under 35 U.S.C. 154(b) by 524 days.

(21) Appl. No.: 11/587,549

(22) PCT Filed: Apr. 27, 2005

(86) PCT No.: PCT/US2005/014202
§ 371 (c)(1),
(2), (4) Date: Apr. 13, 2007

(87) PCT Pub. No.: WO2006/033672
PCT Pub. Date: Mar. 30, 2006

(65) Prior Publication Data
US 2007/0231347 A1 Oct. 4, 2007

Related U.S. Application Data

(60) Provisional application No. 60/565,892, filed on Apr. 28, 2004.

(51) Int. Cl.
A61K 39/12 (2006.01)
C07K 14/005 (2006.01)
C12N 7/00 (2006.01)
C12N 15/86 (2006.01)
A61K 39/00 (2006.01)

(52) U.S. Cl.
CPC ............ *A61K 39/12* (2013.01); *C07K 14/005* (2013.01); *C12N 7/00* (2013.01); *C12N 15/86* (2013.01); *A61K 2039/5254* (2013.01); *A61K 2039/5256* (2013.01); *A61K 2039/5258* (2013.01); *A61K 2039/545* (2013.01); *A61K 2039/57* (2013.01); *C12N 2710/10343* (2013.01); *C12N 2710/10362* (2013.01); *C12N 2750/14043* (2013.01); *C12N 2760/14122* (2013.01); *C12N 2760/14134* (2013.01)

(58) Field of Classification Search
None
See application file for complete search history.

(56) References Cited

U.S. PATENT DOCUMENTS

| 5,856,152 | A | 1/1999 | Wilson |
|---|---|---|---|
| 5,866,552 | A | 2/1999 | Wilson |
| 5,871,982 | A | 2/1999 | Wilson |
| 6,001,557 | A | 12/1999 | Wilson |
| 6,083,716 | A | 7/2000 | Wilson |
| 6,203,975 | B1 | 3/2001 | Wilson |
| 6,251,677 | B1 | 6/2001 | Wilson |
| 6,387,368 | B1 | 5/2002 | Wilson |
| 6,759,237 | B1 | 7/2004 | Wilson |
| 7,105,345 | B2 | 9/2006 | Wilson |
| 7,247,472 | B2 * | 7/2007 | Wilson et al. ............. 435/320.1 |
| 2003/0138772 | A1 | 7/2003 | Gao et al. |
| 2003/0228282 | A1 | 12/2003 | Gao et al. |
| 2004/0057931 | A1 | 3/2004 | Wilson |
| 2004/0057933 | A1 | 3/2004 | Wilson |
| 2004/0136963 | A1 | 7/2004 | Wilson |
| 2005/0069866 | A1 | 3/2005 | Wilson |
| 2005/0265974 | A1 * | 12/2005 | Pau et al. ..................... 424/93.2 |
| 2006/0204479 | A1 | 9/2006 | Wilson |
| 2008/0090281 | A1 | 4/2008 | Wilson |
| 2009/0215871 | A1 | 8/2009 | Wilson |

FOREIGN PATENT DOCUMENTS

| WO | WO 96/13597 A3 | 5/1996 |
|---|---|---|
| WO | WO 96/13598 A2 | 5/1996 |
| WO | WO 98/09657 A2 | 3/1998 |
| WO | WO 98/10087 A1 | 3/1998 |
| WO | WO 00/28061 A3 | 5/2000 |
| WO | WO 03/037275 A2 | 5/2003 |
| WO | WO 03/042397 A2 | 5/2003 |
| WO | WO 03/046124 A2 | 6/2003 |
| WO | WO 03/052051 A2 | 6/2003 |
| WO | WO 03/077859 A2 | 9/2003 |
| WO | WO 2004/055187 * | 1/2004 |
| WO | WO 2005/033321 A2 | 4/2005 |
| WO | WO 2006/033672 A2 | 3/2006 |

OTHER PUBLICATIONS

Chirmule et al, Role of E4 in Eliciting CD4 T-Cell and B-Cell Responses to Adenovirus Vectors Delivered to Murine and Nonhuman Primate Lungs, Journal of Virology, vol. 72, No. 7, pp. 6138-6145, (Jul. 1998) XP-002370669.
Pinto et al, Induction of CD8$^+$ T Cells to an HIV-1 Antigen Through a Prime Boost Regimen with Heterologous E1-Deleted Adenoviral Vaccine Carriers, The Journal of Immunology, vol. 171, No. 12, pp. 6774-6779, (Dec. 15, 2003) XP-002363607.
Russell, Update on Adenovirus and its Vectors, Journal of General Virology, 81, pp. 2573-2604, (Aug. 2000).
Wang et al, Persistent Transgene Expression in Mouse Liver following in Vivo Gene Transfer with a ΔE1/ΔE4 Adenovirus Vector, Gene Therapy, vol. 4, pp. 393-400, (May 1997) XP-000938040.
Wilson, Adenovirus-Mediated Gene Transfer to Liver, Advanced Drug Delivery Reviews, vol. 46, No. 1-3, pp. 205-209, (Mar. 1, 2001), XP-002370668.
US Office Action dated Dec. 28, 2006 with Response.
US Office Action dated Jun. 11, 2007 with Response.
(Continued)

*Primary Examiner* — Benjamin P Blumel
(74) *Attorney, Agent, or Firm* — Howson & Howson

(57) ABSTRACT

An immunization regimen is provided which involves priming with an E1, E4-deleted adenovirus and boosting with an E1-deleted adenovirus. The second administered adenovirus has a capsid of a serotype which is not cross-reactive with the previously administered adenovirus. Further, a product containing the adenoviruses necessary to perform the immunization regimen is provided.

11 Claims, No Drawings

(56) References Cited

OTHER PUBLICATIONS

Communication from EP Application No. 05 816 312.2 with response dated Oct. 31, 2008.
Written opinion of the International Searching Authority dated Mar. 15, 2006.
Office Action dated Jul. 23, 2010 with Response and Amendment from corresponding U.S. Appl. No. 11/820,439.
Office Action dated Oct. 15, 2010 from corresponding U.S. Appl. No. 11/978,477.
Office Action dated Mar. 5, 2010 from corresponding U.S. Appl. No. 11/978,477.
EP Examination Report dated Jul. 23, 2010 from corresponding European Patent Application No. 05 816 312.2.
Response to Office Action issued Jul. 23, 2010 on related U.S. Appl. No. 11/820,439, dated Jan. 23, 2011.
Office Action issued on related U.S. Appl. No. 11/820,439, dated Apr. 11, 2011.
Response to Office Action issued Apr. 11, 2011 on related U.S. Appl. No. 11/820,439, dated Jul. 5, 2011.
Notice of Allowance issued on related U.S. Appl. No. 11/820,439, dated Oct. 3, 2012.
Office Action issued on corresponding Canadian Patent Application No. 2,563,500, dated Feb. 8, 2012.
Office Action issued on corresponding Canadian Patent Application No. 2,563,500, dated Nov. 21, 2012.
Office Action issued on corresponding Canadian Patent Application No. 2,563,500, dated Nov. 4, 2013.
Office Action issued on corresponding Canadian Patent Application No. 2,563,500, dated Dec. 10, 2014.
Office Action issued on corresponding Japanese Patent Application No. 2007-510871, dated Jan. 18, 2011.
Final Office Action issued on corresponding Japanese Patent Application No. 2007-510871, dated Oct. 4, 2011.
Final Office Action issued on corresponding Japanese Patent Application No. 2007-510871, dated Feb. 4, 2014.
Trial Decision issued on corresponding Japanese Patent Application No. 2007-510871, dated Aug. 27, 2014.
Response to Examination Report issued on corresponding European Patent Application No. 05816312.2, dated Jan. 31, 2011.
Oral Proceedings and corresponding submissions issued on corresponding European Patent Application No. 05816312.2, dated Jul. 12, 2012-Apr. 12, 2013.

\* cited by examiner

IMMUNIZATION REGIMEN WITH E4-DELETED ADENOVIRUS PRIME AND E1-DELETED ADENOVIRUS BOOST

CROSS-REFERENCE TO RELATED APPLICATIONS

This is a national stage application under 35 U.S.C. 371 of PCT/US05/014202, filed Apr. 27, 2005 which claims the benefit under 35 U.S.C. 119(e) of the priority of U.S. Patent Application No. 60/565,892, filed Apr. 28, 2004.

BACKGROUND OF THE INVENTION

Adenovirus is a double-stranded DNA virus with a genome size of about 36 kilobases (kb), which has been widely used for gene transfer applications due to its ability to achieve highly efficient gene transfer in a variety of target tissues and large transgene capacity. Conventionally, E1 genes of adenovirus are deleted and replaced with a transgene cassette consisting of the promoter of choice, cDNA sequence of the gene of interest and a poly A signal, resulting in a replication defective recombinant virus.

Adenoviruses have a characteristic morphology with an icosahedral capsid consisting of three major proteins, hexon (II), penton base (III) and a knobbed fibre (IV), along with a number of other minor proteins, VI, VIII, IX, IIIa and IVa2 [W. C. Russell, *J. Gen Virol.*, 81:2573-2604 (November 2000)]. The virus genome is a linear, double-stranded DNA with a terminal protein attached covalently to the 5' termini, which have inverted terminal repeats (ITRs). The virus DNA is intimately associated with the highly basic protein VII and a small peptide termed mu. Another protein, V, is packaged with this DNA-protein complex and provides a structural link to the capsid via protein VI. The virus also contains a virus-encoded protease, which is necessary for processing of some of the structural proteins to produce mature infectious virus.

Recombinant adenoviruses have been described for delivery of molecules to host cells to induce an immune response. See, U.S. Pat. No. 6,083,716, which provides adenoviral vectors derived from the two chimpanzee adenoviruses, C1 and C68 (also termed Pan 9) and International Patent Publication No. WO 02/33645 [Pan 5, Pan6, Pan7-derived vectors].

What is needed in the vaccine field is method of immunizing that will induce a strong immune response to a target with minimal responses to the vaccine carrier.

SUMMARY OF THE INVENTION

The methods of the invention involve delivering one or more selected heterologous gene(s) to a mammalian patient by administering an E1,E4-deleted adenovirus, followed by an E1-deleted adenovirus. Suitably, the second adenovirus administered has a capsid which is different than the previously administered adenovirus. Suitably, the boosting adenovirus contains a product that is the same, or cross-reactive, with that delivered via by the priming composition.

Without being bound by theory, it is believed that because the first vector is lacking adenovirus E4 sequences, which contain CTL epitopes, the immune response to subsequent adenovirus administration is modulated. Thereby, the method of the invention provides a priming of the immune response to the product carried by the adenoviruses, without a concomitant priming of an immune response to the adenovirus carrier.

These and other embodiments and advantages of the invention are described in more detail below.

DETAILED DESCRIPTION OF THE INVENTION

Thus, the invention provides a method of specifically inducing a cellular and/or humoral immune response by sequentially administering an adenovirus lacking a functional E1 and E4 region and an adenovirus lacking a functional E1 region. Each of the adenoviruses contains a heterologous expression cassette comprising a nucleic acid sequence encoding a product for inducing an immune response under the control of regulatory control sequences which direct expression of the product. The products carried by the priming adenovirus and the boosting adenovirus may be the same. Alternatively, the products carried by the priming adenovirus and the boosting adenovirus differ, but the immune response to product of the boosting adenovirus is primed by the product of the earlier adenovirus.

In one embodiment, the encoded products are the same, in order to provide a prime/boost effect to the product, which induces immunity to the target (e.g., disease-causing pathogen) from which the product is derived, or a cross-reactive target. In one embodiment, the regulatory control elements and other elements of the heterologous expression cassette differ in the adenoviruses administered. Suitably, the second administered adenovirus has a capsid which differs immunologically from the capsid of the first administered adenovirus.

As used herein, an adenovirus having a functional deletion in the E1 region is replication-defective and is incapable of expressing the gene products of this region, including the E1a and E1b gene products.

The term "functionally deleted" or "functional deletion" means that a sufficient amount of the gene region is removed or otherwise damaged, e.g., by mutation or modification, so that the gene region is no longer capable of producing functional products of gene expression. If desired, the entire gene region may be removed. Other suitable sites for gene disruption or deletion are discussed elsewhere in the application.

According to the present invention, the adenoviruses containing an E4-deletion are functionally deleted of one or more of the open reading frames (ORFs) of E4 (e.g., ORF 1, ORF2, ORF3, ORF4, ORF5, ORF6 and ORF7). In one embodiment, the construct contains a functional deletion of each of the E4 ORFs. In another embodiment, a combination of one or more of these ORFs is functionally deleted, and preferably, completely absent sequences in the adenoviral construct used in the method of the invention.

In one embodiment, the combination regimen of the invention involves administration of a first adenoviral vector having a capsid protein of a first serotype and subsequent administration of at least one additional adenoviral vector that has a capsid protein which is immunologically distinct from the first, priming, adenoviral vector.

As used herein, a capsid protein is immunologically distinct from another capsid protein if it can be administered to a subject at a level which permits sufficient infection of the target host cells in the absence of an immune response which prevents infection with the second capsid protein (e.g., a clearing neutralizing antibody response). Suitably, the capsid proteins of a boosting adenoviral vector(s) are from a serologically distinct source from the capsid protein of the priming adenoviral vector(s). However, in other embodiments, the capsid proteins of the priming (and optionally, boosting) adenoviral vectors can be delivered without regard to serological distinctiveness, if the native antibody epitopes of the capsid proteins are masked, modified, or otherwise neutralized (e.g., by co-administration of an exogenous molecule).

For example, a vector derived from a simian adenovirus (e.g., C5, C7 or C9), may be used to prime an Ad5 vector, or vice versa (i.e., an Ad5 prime to a C5, C7 or C9 boost). In another embodiment, a vector derived from chimpanzee adenovirus serotype C1 can boost a prime delivered by a simian C5, C7 or C9 vector, or vice versa (i.e., a C1 prime followed by a C5, C7 or C9 boost). Still other prime-boost combinations will be readily apparent to one of skill in the art.

Without wishing to be bound by theory, the inventors have found that removal of adenoviral early genes from a priming administration of an adenoviral vector followed by a boosting administration of a second adenoviral vector assists reduces or eliminates the immune response to the vector. Suitably, the vector delivered in the priming step lacks the ability to express the adenoviral E4 ORF products. In other embodiments, the priming vector further lacks the ability to express the adenoviral E1a products, the E1b gene products, the E2a gene products, and the E2b gene products. Currently, elimination of E3 is desirable to permit insertion of an expression cassette. However, E3 is believed to be implicated in modulation of host immune response to the adenovirus, and thus, may be retained. In one embodiment, the E3 gene product is expressed under the control of a heterologous promoter, to avoid down-regulation of the native E3 promoter which requires E1 expression.

I. Adenoviral Vectors

A. Serotypes

Suitably, these adenoviral vectors of the invention contain one or more adenoviral elements derived from a selected adenoviral genome. In one embodiment, the vectors contain adenoviral ITRs from one selected serotype and additional adenoviral sequences from the same adenoviral serotype. In another embodiment, the vectors contain adenoviral sequences that are derived from a different adenoviral serotype than that which provides the ITRs. As defined herein, a pseudotyped adenovirus refers to an adenovirus in which the capsid protein of the adenovirus is from a different serotype than the serotype which provides the ITRs.

The selection of the serotype of the ITRs and the serotype of any other adenoviral sequences present in vector is not a limitation of the present invention. A variety of adenovirus strains are available from the American Type Culture Collection, Manassas, Va., or available by request from a variety of commercial and institutional sources. Further, the sequences of many such strains are available from a variety of databases including, e.g., PubMed™ and GenBank™. Homologous adenovirus vectors prepared from other simian or from human adenoviruses are described in the published literature [see, for example, U.S. Pat. No. 5,240,846]. The adenovirus sequences may be obtained from any known adenovirus serotype, such as serotypes C, D, 1-40, and particularly 2, 3, 4, 5, 7, 12 and 40, and further including any of the presently identified human types. The DNA sequences of a number of adenovirus types are available from Gen-Bank™ database, including type Ad5 [GenBank Accession No. M73260]. Similarly adenoviruses known to infect non-human animals (e.g., simians) may also be employed in the vector constructs of this invention. See, e.g., the sequences identified herein. See, e.g., U.S. Pat. No. 6,083,716.

In one embodiment, at least one of the adenoviruses used in the invention is derived from a non-human primate. Examples of suitable non-human primate sequences including simian adenoviruses, such as, Pan5 (also C5), Pan6 (also C6), Pan7 (also C7), SV1, SV25, SV39 [see, International Patent Publication No. WO 02/33645, incorporated by reference], Pan 9 (also C68) and C1 [U.S. Pat. No. 6,083,716, incorporated by reference], and SA18 [U.S. patent application Ser. No. 10/465,302 and its international counterpart, WO 2005/001103, incorporated by reference].

Examples of other adenovirus serotype that may be useful in the method of the invention includes, e.g., serotype 34 [WO 2004/4097016], serotype 24 [WO 2004/083418]; and serotype 35 [EP 1054064].

The invention further encompasses pseudotyped adenoviruses, chimeric and hybrid adenoviral vectors. See, e.g., U.S. patent application Ser. No. 10/465,302 and its international counterpart, WO 2005/001103, incorporated by reference. See, also, US 2005/032045; WO 2004/108755; US 2004/081637.

A simian adenoviral having a modified capsid can be used as either the prime or boost. In one embodiment, the modification to the adenovirus renders it immunologically and/or serologically distinct from the parental capsid serotype. Thus, such a modified capsid can be used in a regimen with the parental capsid or in a regimen with another adenoviral type. In other embodiments, the modification to the adenovirus provides another advantage, e.g., increased induction of immune response or targeting of specific cell types. Methods of modifying adenoviruses have been described. See, e.g., T P Cripe, et al., Cancer Res, 61(7): 2953-60 (April 2001) (fiber knob modifications); S C Stevenson, et al., J Virol, 71(6):4782-90 (modified fiber protein); C. Volpers, et al., J Virol, 77(3):2093-104 (February 2003); S. Worgal, et al, J. Virol., 78(5):2572-80 (March 2004) (modified capsid enhances dendtritic cell infection and transgene-specific cellular immune responses); M. Wang, et. al., Gyncol. Oncol., 96(2):341-8 (February 2005).

However, the invention is not limited to the selection of the capsid serotype or the origin of other adenoviral elements present in the vector.

B. Adenoviral Elements

The adenoviral particles or vectors used in the present invention are composed of adenovirus protein capsids having packaged therein an expression cassette carrying a product to be expressed in the host and sufficient viral elements to permit delivery of the expression cassette to an infected host cell. Desirably, these adenoviral vectors are replication-defective, thereby avoiding replication in a host cell.

In one embodiment, these adenoviral particles contain 5' adenoviral cis-elements and 3' adenoviral cis-elements at the extreme 5' and 3' termini of the adenovirus, respectively. The 5' end of the adenoviral genome contains the 5' cis-elements necessary for packaging and replication; i.e., the 5' inverted terminal repeat (ITR) sequences (which functions as origins of replication) and the 5' packaging enhancer domains (that contain sequences necessary for packaging linear Ad genomes and enhancer elements for the E1 promoter). The 3' end of the adenoviral genome includes the 3' cis-elements (including the ITRs) necessary for packaging and encapsidation.

An adenoviral vector used in the invention may contain additional adenoviral sequences, or may be at least functionally deleted in one or more adenoviral gene regions. In one embodiment, an adenoviral vector used in the invention will contain the E2 region or a functional portion thereof (e.g., the region encoding E2a and/or E2b), and one or more of the late genes, e.g., L1, L2, L3, L4 and L5. In some embodiments, the adenovirus vectors used in the invention may contain all or a portion of the E4 region (e.g., the E4 ORF6).

For example, all or a portion of the adenovirus delayed early gene E3 may be eliminated from the simian adenovirus sequence which forms a part of the viral vector. The function of simian E3 is believed to be irrelevant to the function and production of the recombinant virus particle.

For example, an E1-deleted Ad vector can be constructed having a deletion of at least the ORF6 region of the E4 gene, and more desirably because of the redundancy in the function of this region, the entire E4 region. Still another vector of this invention contains a deletion in the delayed early gene E2a. Suitably, these vectors retain the late genes (i.e., L1, L2, L3, L4, and L5), and other elements essential for packaging of adenoviral vectors into viral particles. Deletions may also be made in the intermediate genes IX and IVa$_2$ for some purposes. Other deletions may be made in the other structural or non-structural adenovirus genes. The above discussed deletions may be used individually, i.e., an adenovirus sequence for use in the present invention may contain deletions in only a single region. Alternatively, deletions of entire genes or portions thereof effective to destroy their biological activity may be used in any combination. For example, in one exemplary vector, the adenovirus sequence may have deletions of the E1 genes and one or more of the E4 ORFs, or the E1 genes, with or without deletion of E3, and so on.

C. Vector Elements

The methods employed for the selection of the antigen or immunogen (i.e., product) and the sequences encoding same, the cloning and construction of the "heterologous expression cassette" and its insertion into the viral vector are within the skill in the art given the teachings provided herein. According to the present invention, the heterologous expression cassette can be located in the site of any native adenoviral region, which is located between the 5' and 3' adenovirus ITRs. In one embodiment, the heterologous expression cassette is located in the native E1 region of the adenoviral vector. In another embodiment, the heterologous expression cassette is located in the native E3 region. In other embodiments, the gene product is expressed from the native E1 region of the adenoviral vector, or from the native E3 region of the adenoviral vector, and is operably linked to regulatory control elements which are non-contiguous with the sequences encoding the gene product.

In yet another embodiment, the adenoviral vector carries more than one heterologous expression cassette, which can be inserted into multiple deletion sites in the adenoviral genome. This invention is not limited by the direction in which the expression cassette is inserted, which may be 5'-3', or 3'-5', relative to the normal reading frame of the adenoviral genome flanking the insertion site of the expression cassette.

1. The Nucleic Acid Sequence

The expression cassette contains nucleic acid sequence, heterologous to the vector sequences flanking the sequence, which encodes a polypeptide, protein, or other product, of interest. Suitably, this product is an immunogen or antigen. The nucleic acid coding sequence is operatively linked to regulatory components in a manner which permits transcription, translation, and/or expression of the product in a host cell. Suitable nucleic acid sequences and products may be readily selected by one of skill in the art. The selection of these elements is not a limitation of this invention. Optionally, any of the nucleic acid coding sequences described herein can be provided with a tag or other marker, which allows detection of the sequence (or encoded product) following infection of the vector into host cells. Suitable tags are known to those of skill in the art and are not a limitation of the present invention.

2. Regulatory Elements

In addition to the major elements identified above for the expression cassette, the vector also includes conventional control elements which are operably linked to the sequences encoding the product in a manner that permits transcription, translation and/or expression of the product in a cell infected with the virus used in the invention. As used herein, "operably linked" sequences include both expression control sequences that are contiguous with the product (e.g., gene) of interest and expression control sequences that act in trans or at a distance to control expression the product.

Expression control sequences include appropriate transcription initiation, termination, promoter and enhancer sequences; efficient RNA processing signals such as splicing and polyadenylation (polyA) signals; sequences that stabilize cytoplasmic mRNA; sequences that enhance translation efficiency (i.e., Kozak consensus sequence); sequences that enhance protein stability; and when desired, sequences that enhance secretion of the encoded product. A great number of expression control sequences, including promoters which are native, constitutive, inducible and/or tissue-specific, are known in the art and may be utilized.

Examples of constitutive promoters include, without limitation, the retroviral Rous sarcoma virus (RSV) LTR promoter (optionally with the RSV enhancer), the cytomegalovirus (CMV) promoter (optionally with the CMV enhancer) [see, e.g., Boshart et al, *Cell*, 41:521-530 (1985)], the SV40 promoter, the dihydrofolate reductase promoter, the β-actin promoter, the phosphoglycerol kinase (PGK) promoter, and the EF1α promoter [Invitrogen].

In another embodiment, the native promoter for the gene will be used. The native promoter may be preferred when it is desired that expression of the product should mimic the native expression. The native promoter may be used when expression of the product must be regulated temporally or developmentally, or in a tissue-specific manner, or in response to specific transcriptional stimuli. In a further embodiment, other native expression control elements, such as enhancer elements, polyadenylation sites or Kozak consensus sequences may also be used to mimic the native expression.

Another embodiment of the expression cassette includes a nucleic acid sequence encoding a product operably linked to a tissue-specific promoter. For instance, if expression in skeletal muscle is desired, a promoter active in muscle should be used. These include the promoters from genes encoding skeletal β-actin, myosin light chain 2A, dystrophin, muscle creatine kinase, as well as synthetic muscle promoters with activities higher than naturally occurring promoters (see Li et al., *Nat. Biotech.*, 17:241-245 (1999)). Examples of promoters that are tissue-specific are known for liver (albumin, Miyatake et al., *J. Virol.*, 71:5124-32 (1997); hepatitis B virus core promoter, Sandig et al., *Gene Ther.*, 3:1002-9 (1996); alpha-fetoprotein (AFP), Arbuthnot et al., *Hum. Gene Ther.*, 7:1503-14 (1996)), bone osteocalcin (Stein et al., *Mol. Biol. Rep.*, 24:185-96 (1997)); bone sialoprotein (Chen et al., *J. Bone Miner. Res.*, 11:654-64 (1996)), lymphocytes (CD2, Hansal et al, *J. Immunol.*, 161:1063-8 (1998); immunoglobulin heavy chain; T cell receptor chain), neuronal such as neuron-specific enolase (NSE) promoter (Andersen et al., *Cell. Mol. Neurobiol.*, 13:503-15 (1993)), neurofilament light-chain gene (Piccioli et al., *Proc. Natl. Acad. Sci. USA*, 88:5611-5 (1991)), and the neuron-specific vgf gene (Piccioli et al, *Neuron*, 15:373-84 (1995)), among others.

Optionally, vectors carrying sequences encoding immunogenic products may also include tags or markers to allow one of skill in the art to detect the expression of a variety of proteins. The addition of these epitope tags can in some cases obviate the need to generate specific antisera to each individual protein.

These vectors are generated using the techniques and sequences provided herein, in conjunction with techniques known to those of skill in the art. Such techniques include conventional cloning techniques of cDNA such as those described in texts [Sambrook et al, Molecular Cloning: A Laboratory Manual, Cold Spring Harbor Press, Cold Spring Harbor, N.Y.], use of overlapping oligonucleotide sequences of the adenovirus genomes, polymerase chain reaction, and any suitable method which provides the desired nucleotide sequence.

As stated above, while in one embodiment, the immunization regimen of the invention involves sequential delivery of the same immunogenic product via different adenoviral vectors, the expression cassette used in the vectors of any given regimen need not be the same. In fact, the expression cassette can contain regulatory sequences for the immunogenic product and/or vector elements different. Thus, the selection of these regulatory and vector elements are not a limitation of the invention even within the contact of an immunization regimen for a selected subject.

D. Production of Adenoviral Particles

A variety of production methods for adenoviral particles is known to those of skill in the art. The selection of appropriate production methods is not a limitation of the present invention. See, e.g., U.S. Pat. No. 6,083,716; International Patent Publication No. WO 02/33645; and U.S. patent application Ser. No. 10/465,302, which are incorporated by reference. Briefly, an adenoviral vector lacking the ability to express any essential adenoviral gene products (e.g., E1a, E1b, E2a, E2b, E4 ORF6) can be cultured in the presence of the missing adenoviral gene products which are required for viral infectivity and propagation of an adenoviral particle. These helper functions may be provided by culturing the adenoviral vector in the presence of one or more helper constructs (e.g., a plasmid or virus) or a packaging host cell. See, for example, the techniques described for preparation of a "minimal" human Ad vector in International Patent Application No. WO 96/13597, published May 9, 1996, and incorporated herein by reference.

Regardless of whether the adenoviral vectors contains only the minimal Ad sequences, or the entire Ad genome with only functional deletions in the E1 and/or E3 regions, in one embodiment, the recombinant virus contains a capsid derived from a simian adenovirus. Alternatively, in other embodiments, recombinant pseudotyped adenoviruses may be used in the methods of the invention. Such pseudotyped adenoviruses utilize adenovirus capsid proteins in which a nucleic acid molecule carrying adenovirus sequences from another serotype have been packaged. These adenoviral vectors useful in the invention may be produced using methods that are known to those of skill in the art.

1. Helper Viruses

Thus, depending upon the adenovirus gene content of the viral vectors employed to carry the expression cassette, a helper adenovirus or non-replicating virus fragment may be necessary to provide sufficient adenovirus gene sequences necessary to produce an infective recombinant viral particle containing the expression cassette. Useful helper viruses contain selected adenovirus gene sequences not present in the adenovirus vector construct and/or not expressed by the packaging cell line in which the vector is transfected. In one embodiment, the helper virus is replication-defective and contains a variety of adenovirus genes in addition to the sequences described above. Such a helper virus is desirably used in combination with an E1-expressing cell line.

Helper viruses may also be formed into poly-cation conjugates as described in Wu et al, *J. Biol. Chem.*, 264: 16985-16987 (1989); K. J. Fisher and J. M. Wilson, *Biochem. J.*, 299:49 (Apr. 1, 1994). Helper virus may optionally contain a second reporter expression cassette. A number of such reporter genes are known to the art. The presence of a reporter gene on the helper virus which is different from the gene product on the adenovirus vector allows both the Ad vector and the helper virus to be independently monitored. This second reporter is used to enable separation between the resulting recombinant virus and the helper virus upon purification.

2. Complementation Cell Lines

To generate recombinant adenoviruses (Ad) deleted in any of the genes described above, the function of the deleted gene region, if essential to the replication and infectivity of the virus, must be supplied to the recombinant virus by a helper virus or cell line, i.e., a complementation or packaging cell line. In many circumstances, a cell line expressing the human E1 can be used to transcomplement the chimp Ad vector. This is particularly advantageous because, due to the diversity between the chimp Ad sequences of the invention and the human AdE1 sequences found in currently available packaging cells, the use of the current human E1-containing cells prevents the generation of replication-competent adenoviruses during the replication and production process. However, in certain circumstances, it will be desirable to utilize a cell line which expresses the E1 gene products can be utilized for production of an E1-deleted simian adenovirus. Such cell lines have been described. See, e.g., U.S. Pat. No. 6,083,716.

If desired, one may utilize the sequences provided herein to generate a packaging cell or cell line that expresses, at a minimum, the adenovirus E1 gene under the transcriptional control of a promoter for expression in a selected parent cell line. Inducible or constitutive promoters may be employed for this purpose. Examples of such promoters are described in detail elsewhere in this specification. A parent cell is selected for the generation of a novel cell line expressing any desired Ad gene. Without limitation, such a parent cell line may be derived from HeLa [ATCC Accession No. CCL 2], A549 [ATCC Accession No. CCL 185], HEK 293, KB [CCL 17], Detroit [e.g., Detroit 510, CCL 72] and WI-38 [CCL 75] cells, among others. These cell lines are all available from the American Type Culture Collection, 10801 University Boulevard, Manassas, Va. 20110-2209. Other suitable parent cell lines may be obtained from other sources.

Such E1-expressing cell lines are useful in the generation of recombinant adenovirus E1 deleted vectors. Additionally, or alternatively, the invention provides cell lines that express one or more simian adenoviral gene products, e.g., E1a, E1b, E2a, and/or E4 ORF6, can be constructed using essentially the same procedures for use in the generation of recombinant simian viral vectors. Such cell lines can be utilized to transcomplement adenovirus vectors deleted in the essential genes that encode those products. The preparation of a host cell according to this invention involves techniques such as assembly of selected DNA sequences. This assembly may be accomplished by direct cloning techniques [G. Gao et al, *Gene Ther.* 2003 October; 10(22):1926-1930; US Patent Publication No. 2003-0092161-A, May 15, 2003; International Patent Application No. PCT/US03/12405]. Other suitable techniques include cDNA and genomic cloning, which are well known and are described in Sambrook et al., cited above, use of overlapping oligonucleotide sequences of the adenovirus genomes, combined with polymerase chain reaction, synthetic methods, and any other suitable methods which provide the desired nucleotide sequence.

In still another alternative, the essential adenoviral gene products are provided in trans by the adenoviral vector and/or helper virus. In such an instance, a suitable host cell can be selected from any biological organism, including prokaryotic (e.g., bacterial) cells, and eukaryotic cells, including, insect cells, yeast cells and mammalian cells. Particularly desirable host cells are selected from among any mammalian species, including, without limitation, cells such as A549, WEHI, 3T3, 10T1/2, HEK 293 cells or PERC6 (both of which express functional adenoviral E1) [Fallaux, F J et al, (1998), *Hum Gene Ther,* 9:1909-1917], Saos, C2C12, L cells, HT1080, HepG2 and primary fibroblast, hepatocyte and myoblast cells derived from mammals including human, monkey, mouse, rat, rabbit, and hamster. The selection of the mammalian species providing the cells is not a limitation of this invention; nor is the type of mammalian cell, i.e., fibroblast, hepatocyte, tumor cell, etc.

3. Assembly of Viral Particle and Transfection of a Cell Line

Generally, when delivering the vector comprising the expression cassette by transfection, the vector is delivered in an amount from about 5 μg to about 100 μg DNA, and preferably about 10 to about 50 μg DNA to about $1\times10^4$ cells to about $1\times10^{13}$ cells, and preferably about $10^5$ cells. However, the relative amounts of vector DNA to host cells may be adjusted, taking into consideration such factors as the selected vector, the delivery method and the host cells selected.

The vector may be any vector known in the art or disclosed above, including naked DNA, a plasmid, phage, transposon, cosmids, episomes, viruses, etc. Introduction into the host cell of the vector may be achieved by any means known in the art or as disclosed above, including transfection, and infection. One or more of the adenoviral genes may be stably integrated into the genome of the host cell, stably expressed as episomes, or expressed transiently. The gene products may all be expressed transiently, on an episome or stably integrated, or some of the gene products may be expressed stably while others are expressed transiently.

Furthermore, the promoters for each of the adenoviral genes may be selected independently from a constitutive promoter, an inducible promoter or a native adenoviral promoter. The promoters may be regulated by a specific physiological state of the organism or cell (i.e., by the differentiation state or in replicating or quiescent cells) or by exogenously-added factors, for example.

Introduction of the molecules (as plasmids or viruses) into the host cell may also be accomplished using techniques known to the skilled artisan and as discussed throughout the specification. In preferred embodiment, standard transfection techniques are used, e.g., $CaPO_4$ transfection or electroporation.

Assembly of the selected DNA sequences of the adenovirus (as well as the transgene and other vector elements into various intermediate plasmids, and the use of the plasmids and vectors to produce a recombinant viral particle are all achieved using conventional techniques. Such techniques include direct cloning as has been described [G. Gao et al, *Gene Ther.* 2003 October; 10(22):1926-1930; US Patent Publication No. 2003-0092161-A, May 15, 2003; International Patent Application No. PCT/US03/12405]. Alternatively, cloning techniques of cDNA such as those described in texts [Sambrook et al, cited above], use of overlapping oligonucleotide sequences of the adenovirus genomes, polymerase chain reaction, and any suitable method which provides the desired nucleotide sequence. Standard transfection and co-transfection techniques are employed, e.g., $CaPO_4$ precipitation techniques. Other conventional methods employed include homologous recombination of the viral genomes, plaquing of viruses in agar overlay, methods of measuring signal generation, and the like.

For example, following the construction and assembly of the desired expression cassette-containing viral vector, the vector is transfected in vitro in the presence of a helper virus into the packaging cell line. Homologous recombination occurs between the helper and the vector sequences, which permits the adenovirus-transgene sequences in the vector to be replicated and packaged into virion capsids, resulting in the recombinant viral vector particles. The current method for producing such virus particles is transfection-based. However, the invention is not limited to such methods.

The resulting recombinant adenoviruses are useful in transferring a selected transgene to a selected cell.

II. Formulation of Viral Vectors for Immunization

According to the present invention, recombinant vectors are used in the immunization regimen of the invention for inducing an immune response in a mammalian subject (e.g., a human, simian or non-simian veterinary patient) following ex vivo or in vivo administration. In one embodiment, the immune response is a humoral (i.e., antibody) response to the product expressed by the viral vectors. Depending upon the antigen product expressed, such an antibody response can be specific to the pathogen from which the antigen is derived or cross-reactive with other, related pathogens. In another embodiment, the immune response can be a cellular (e.g., CTL) response. Depending upon the immunogenic product expressed, such a CTL response can be specific to the pathogen from which the immunogen is derived or cross-reactive with other, related pathogens. In still other embodiments, both antibody and CTL response may be induced. However, the method of the invention is advantageous is that it minimizes, and in some cases eliminates, immune response to the viral vector, and particularly, the adenoviral vector.

Thus, the immunization regimens of the invention can be applied either in prophylactic or therapeutic vaccines. Such vaccinal (or other immunogenic) compositions are formulated in a suitable delivery vehicle, as described above. Generally, doses for the immunogenic compositions are in the range defined above for therapeutic compositions. The levels of immunity of the selected gene can be monitored to determine the need, if any, for boosters. Following an assessment of antibody titers in the serum, optional booster immunizations may be desired.

Optionally, a composition of the invention may be formulated to contain viral vectors as described herein, as well as other components, including, e.g. adjuvants, stabilizers, pH adjusters, preservatives and the like. Suitable exemplary preservatives include chlorobutanol, potassium sorbate, sorbic acid, sulfur dioxide, propyl gallate, the parabens, ethyl vanillin, glycerin, phenol, and parachlorophenol.

Suitable chemical stabilizers include gelatin and albumin. Suitable exemplary adjuvants include, among others, immune-stimulating complexes (ISCOMS), LPS analogs including 3-O-deacylated monophosphoryl lipid A (Ribi Immunochem Research, Inc.; Hamilton, Mont.), mineral oil and water, aluminum hydroxide, Amphigen, Avirdine, L121/squalene, muramyl peptides, and saponins, such as Quil A, and any biologically active factor, such as cytokine, an interleukin, a chemokine, a ligands, and optimally combinations thereof. Certain of these biologically active factors can be expressed in vivo, e.g., via a plasmid or viral vector. For example, such an adjuvant can be administered with a priming adenoviral vector.

The viral vectors used in the invention are administered in "an immunogenic amount", that is, an amount of virus that is effective in a route of administration to transfect the desired cells and provide sufficient levels of expression of the selected gene to induce an immune response. Where protective immunity is provided, the viruses are considered to be vaccine compositions useful in preventing infection and/or recurrent disease.

Alternatively, or in addition, the vectors used in the invention may contain nucleic acid sequences encoding a product (e.g., a peptide, polypeptide, or protein) which induces an immune response to a selected immunogen. The immunogenic regimen provided herein is expected to be highly efficacious at inducing cytolytic T cells and antibodies to the inserted heterologous antigenic protein expressed by the vector.

For example, immunogens may be selected from a variety of viral families. Example of desirable viral families against which an immune response would be desirable include, the picornavirus family, which includes the genera rhinoviruses, which are responsible for about 50% of cases of the common cold; the genera enteroviruses, which include polioviruses, coxsackieviruses, echoviruses, and human enteroviruses such as hepatitis A virus; and the genera apthoviruses, which are responsible for foot and mouth diseases, primarily in non-human animals. Within the picornavirus family of viruses, target antigens include the VP1, VP2, VP3, VP4, and VPG. Another viral family includes the calcivirus family, which encompasses the Norwalk group of viruses, which are an important causative agent of epidemic gastroenteritis. Still another viral family desirable for use in targeting antigens for inducing immune responses in humans and non-human animals is the togavirus family, which includes the genera alphavirus, which include Sindbis viruses, Ross-River virus, and Venezuelan, Eastern & Western Equine encephalitis, and rubivirus, including Rubella virus. The flaviviridae family includes dengue, yellow fever, Japanese encephalitis, St. Louis encephalitis and tick borne encephalitis viruses.

Other target antigens may be generated from the Hepatitis C [see, e.g., US Published Patent Application No. US 2003/190606 (Oct. 9, 2003); US 2002/081568 (Jun. 27, 2002)] or the coronavirus family, which includes a number of non-human viruses such as infectious bronchitis virus (poultry), porcine transmissible gastroenteric virus (pig), porcine hemagglutinating encephalomyelitis virus (pig), feline infectious peritonitis virus (cats), feline enteric coronavirus (cat), canine coronavirus (dog), and human respiratory coronaviruses, which may cause the common cold and/or non-A, B or C hepatitis. Additionally, the putative causative agent of sudden acute respiratory syndrome (SARS) is found in the coronavirus family. Within the coronavirus family, target antigens include the E1 (also called M or matrix protein), E2 (also called S or Spike protein), E3 (also called HE or hemagglutin-elterose) glycoprotein (not present in all coronaviruses), or N (nucleocapsid). Still other antigens may be targeted against the rhabdovirus family, which includes the genera vesiculovirus (e.g., Vesicular Stomatitis Virus), and the general lyssavirus (e.g., rabies). Within the rhabdovirus family, suitable antigens may be derived from the G protein or the N protein. The family filoviridae, which includes hemorrhagic fever viruses such as Marburg and Ebola virus, may be a suitable source of antigens. The paramyxovirus family includes parainfluenza Virus Type 1, parainfluenza Virus Type 3, bovine parainfluenza Virus Type 3, rubulavirus (mumps virus), parainfluenza Virus Type 2, parainfluenza virus Type 4, Newcastle disease virus (chickens), rinderpest, morbillivirus, which includes measles and canine distemper, and pneumovirus, which includes respiratory syncytial virus (e.g., the glyco-(G) protein and the fusion (F) protein, for which sequences are available from GenBank).

The influenza virus is classified within the family orthomyxovirus and is a suitable source of antigen (e.g., the HA protein, the N1 protein). The bunyavirus family includes the genera bunyavirus (California encephalitis, La Crosse), phlebovirus (Rift Valley Fever), hantavirus (puremala is a hemahagin fever virus), nairovirus (Nairobi sheep disease) and various unassigned bungaviruses. The arenavirus family provides a source of antigens against LCM and Lassa fever virus. The reovirus family includes the genera reovirus, rotavirus (which causes acute gastroenteritis in children), orbiviruses, and cultivirus (Colorado Tick fever, Lebombo (humans), equine encephalosis, blue tongue).

The retrovirus family includes the sub-family oncorivirinal which encompasses such human and veterinary diseases as feline leukemia virus, HTLVI and HTLVII, lentivirinal (which includes human immunodeficiency virus (HIV), simian immunodeficiency virus (SIV), feline immunodeficiency virus (FIV), equine infectious anemia virus, and spumavirinal). Among the lentiviruses, many suitable antigens have been described and can readily be selected.

Examples of suitable HIV and SIV antigens include, without limitation the gag, pol, Vif, Vpx, VPR, Env, Tat, Nef, and Rev proteins, as well as various fragments thereof. For example, suitable fragments of the Env protein may include any of its subunits such as the gp120, gp140, gp160, gp41, or smaller fragments thereof, e.g., of at least about 8 amino acids in length. Similarly, fragments of the tat protein may be selected. [See, U.S. Pat. No. 5,891,994 and U.S. Pat. No. 6,193,981.] See, also, the HIV and SIV proteins described in D. H. Barouch et al, *J. Virol.*, 75(5):2462-2467 (March 2001), and R. R. Amara, et al, *Science*, 292:69-74 (6 Apr. 2001). In another example, the HIV and/or SIV immunogenic proteins or peptides may be used to form fusion proteins or other immunogenic molecules. See, e.g., the HIV-1 Tat and/or Nef fusion proteins and immunization regimens described in International Patent Publication No. WO 01/54719, published Aug. 2, 2001, International Patent Publication No WO 99/16884, published Apr. 8, 1999; WO 03/011334; US 2003/158134. The invention is not limited to the HIV and/or SIV immunogenic proteins or peptides described herein. In addition, a variety of modifications to these proteins has been described or could readily be made by one of skill in the art. See, e.g., the modified gag protein that is described in U.S. Pat. No. 5,972,596. Further, any desired HIV and/or SIV immunogens may be delivered alone or in combination. Such combinations may include expression from a single vector or from multiple vectors. Optionally, another combination may involve delivery of one or more expressed immunogens with delivery of one or more of the immunogens in protein form. Such combinations are discussed in more detail below.

The papovavirus family includes the sub-family polyomaviruses (BKU and JCU viruses) and the sub-family papillomavirus (associated with cancers or malignant progression of papilloma). Examples of papillomavirus proteins useful as immunogenic products include those derived from the papilloma virus "early" and "late" genes designated E1 to E7, L1 and L2. See, e.g., US Published Patent Application No. 2002/0137720 [Ertl]. Other papillomavirus antigens and combinations thereof have been described. See, e.g., US Published Application No. 2003/129199 (Jul. 10, 2003); US Published Application No. 2002/18221 (Dec. 15, 2002); U.S. Pat. No. 6,342,224.

The adenovirus family includes viruses (EX, AD7, ARD, O.B.) which cause respiratory disease and/or enteritis. The parvovirus family feline parvovirus (feline enteritis), feline panleucopeniavirus, canine parvovirus, and porcine parvovirus. The herpesvirus family includes the sub-family alphaherpesvirinae, which encompasses the genera simplexvirus (HSVI, HSVII), varicellovirus (pseudorabies, varicella zoster) and the sub-family betaherpesvirinae, which includes the genera cytomegalovirus (Human CMV), muromegalovirus) and the sub-family gammaherpesvirinae, which includes the genera lymphocryptovirus, EBV (Burkitts lymphoma), infectious rhinotracheitis, Marek's disease virus, and rhadinovirus. The poxvirus family includes the sub-family chordopoxvirinae, which encompasses the genera orthopoxvirus (Variola (Smallpox) and Vaccinia (Cowpox)), parapoxvirus, avipoxvirus, capripoxvirus, leporipoxvirus, suipoxvirus, and the sub-family entomopoxvirinae. The hepadnavirus family includes the Hepatitis B virus. One unclassified virus which may be suitable source of antigens is the Hepatitis delta virus. Still other viral sources may include avian infectious bursal disease virus and porcine respiratory and reproductive syndrome virus. The alphavirus family includes equine arteritis virus and various Encephalitis viruses.

The present invention may also encompass regimens utilizing product which are useful to immunize a human or non-human animal against other pathogens including bacteria, fungi, parasitic microorganisms or multicellular parasites which infect human and non-human vertebrates, or from a cancer cell or tumor cell. Examples of bacterial pathogens include pathogenic gram-positive cocci include pneumococci; staphylococci; and streptococci. Pathogenic gram-negative cocci include *meningococcus; gonococcus*. Pathogenic enteric gram-negative bacilli include enterobacteriaceae; *pseudomonas*, acinetobacteria and eikenella; melioidosis; *salmonella; shigella; haemophilus (Haemophilus influenzae, Haemophilus somnus)*; *moraxella; H. ducreyi* (which causes chancroid); *brucella; Franisella tularensis* (which causes tularemia); *yersinia (pasteurella); streptobacillus moniliformis* and *spirillum*. Gram-positive bacilli include *listeria monocytogenes; erysipelothrix rhusiopathiae; Corynebacterium diphtheria (diphtheria); cholera; B. anthracis* (anthrax); donovanosis (granuloma inguinale); and bartonellosis. Diseases caused by pathogenic anaerobic bacteria include tetanus; botulism; other clostridia; tuberculosis; leprosy; and other mycobacteria.

Examples of specific bacterium species are, without limitation, *Streptococcus pneumoniae, Streptococcus pyogenes, Streptococcus agalactiae, Streptococcus faecalis, Moraxella catarrhalis, Helicobacter pylori, Neisseria meningitidis, Neisseria gonorrhoeae, Chlamydia trachomatis, Chlamydia pneumoniae, Chlamydia psittaci, Bordetella pertussis, Salmonella typhi, Salmonella typhimurium, Salmonella choleraesuis, Escherichia coli, Shigella, Vibrio cholerae, Corynebacterium diphtheriae, Mycobacterium tuberculosis, Mycobacterium avium, Mycobacterium intracellulare* complex, *Proteus mirabilis, Proteus vulgaris, Staphylococcus aureus, Clostridium tetani, Leptospira interrogans, Borrelia burgdorferi, Pasteurella haemolytica, Pasteurella multocida, Actinobacillus pleuropneumoniae* and *Mycoplasma gallisepticum*.

Pathogenic spirochetal diseases include syphilis; treponematoses: yaws, pinta and endemic syphilis; and leptospirosis. Other infections caused by higher pathogen bacteria and pathogenic fungi include actinomycosis; nocardiosis; cryptococcosis (*Cryptococcus*), blastomycosis (*Blastomyces*), histoplasmosis (*Histoplasma*) and coccidioidomycosis (*Coccidiodes*); candidiasis (*Candida*), aspergillosis (*Aspergillis*), and mucormycosis; sporotrichosis; paracoccidiodomycosis, petriellidiosis, torulopsosis, mycetoma and chromomycosis; and dermatophytosis. Rickettsial infections include Typhus fever, Rocky Mountain spotted fever, Q fever, and Rickettsialpox. Examples of *mycoplasma* and chlamydial infections include: *mycoplasma pneumoniae*; lymphogranuloma venereum; psittacosis; and perinatal chlamydial infections. Pathogenic eukaryotes encompass pathogenic protozoans and helminths and infections produced thereby include: amebiasis; malaria; leishmaniasis (e.g., caused by *Leishmania major*); trypanosomiasis; toxoplasmosis (e.g., caused by *Toxoplasma gondii*); *Pneumocystis carinii; Trichans; Toxoplasma gondii*; babesiosis; giardiasis (e.g., caused by *Giardia*); trichinosis (e.g., caused by *Trichomonas*); filariasis; schistosomiasis (e.g., caused by *Schistosoma*); nematodes; trematodes or flukes; and cestode (tapeworm) infections. Other parasitic infections may be caused by *Ascaris, Trichuris, Cryptosporidium*, and *Pneumocystis carinii*, among others.

Many of these organisms and/or toxins produced thereby have been identified by the Centers for Disease Control [(CDC), Department of Heath and Human Services, USA], as agents which have potential for use in biological attacks. For example, some of these biological agents, include, *Bacillus anthracis* (anthrax), *Clostridium botulinum* and its toxin (botulism), *Yersinia pestis* (plague), variola major (smallpox), *Francisella tularensis* (tularemia), and viral hemorrhagic fevers [filoviruses (e.g., Ebola, Marburg], and arenaviruses [e.g., Lassa, Machupo]), all of which are currently classified as Category A agents; *Coxiella burnetti* (Q fever); *Brucella* species (brucellosis), *Burkholderia mallei* (glanders), *Burkholderia pseudomallei* (meloidosis), *Ricinus communis* and its toxin (ricin toxin), *Clostridium perfringens* and its toxin (epsilon toxin), *Staphylococcus* species and their toxins (enterotoxin B), *Chlamydia psittaci* (psittacosis), water safety threats (e.g., *Vibrio cholerae, Crytosporidium parvum*), Typhus fever (*Richettsia powazekii*), and viral encephalitis (alphaviruses, e.g., Venezuelan equine encephalitis; eastern equine encephalitis; western equine encephalitis); all of which are currently classified as Category B agents; and Nipan virus and hantaviruses, which are currently classified as Category C agents. In addition, other organisms, which are so classified or differently classified, may be identified and/or used for such a purpose in the future. It will be readily understood that the viral vectors and other constructs described herein are useful to deliver antigens from these organisms, viruses, their toxins or other by-products, which will prevent and/or treat infection or other adverse reactions with these biological agents.

Administration of the vectors according to the invention to deliver immunogens against the variable region of the T cells elicit an immune response including cytotoxic T-lymphocytes (CTLs) to eliminate those T cells. In rheumatoid arthritis (RA), several specific variable regions of T-cell receptors (TCRs) that are involved in the disease have been characterized. These TCRs include V-3, V-14, V-17 and Vα-17. Thus, delivery of a nucleic acid sequence that encodes at least one of these polypeptides will elicit an immune response that will target T cells involved in RA. In multiple sclerosis (MS), several specific variable regions of TCRs which are involved in the disease have been characterized. These TCRs include V-7 and Vα-10. Thus, delivery of a nucleic acid sequence that encodes at least one of these polypeptides will elicit an immune response that will target T cells involved in MS. In scleroderma, several specific variable regions of TCRs which are involved in the disease have been characterized. These TCRs include V-6, V-8, V-14 and Vα-16, Vα-3C, Vα-7, Vα-14, Vα-15, Vα-16, Vα-28 and Vα-12. Thus, delivery of a recombinant simian adenovirus that encodes at least one of these polypeptides will elicit an immune response that will target T cells involved in scleroderma.

Further, desirable immunogens include those directed to eliciting a therapeutic or prophylactic anti-cancer effect in a vertebrate host, such as, without limitation, those utilizing a cancer antigen or tumor-associated antigen including, without limitation, prostate specific antigen, carcino-embryonic antigen, MUC-1, Her2, CA-125 and MAGE-3.

Suitably, the adenoviral vectors are delivered in a combination regimen involving sequential administration of a functional E1, E4-deleted adenovirus and a functional E1-deleted adenovirus. The regimen of the invention can be administered at various sites in the body in a dose dependent manner, which depends on the indication to which the desired immune response is being targeted.

In one embodiment, the invention provides for use of the adenoviral vectors of the invention in the preparation of a medicament for specifically inducing an immune response in a subject. In another embodiment, the vectors are prepared for sequential administration.

The invention is not limited to the amount or situs of injection(s) or to the pharmaceutical carrier. The regimen involves a priming step and a boosting step. Each step may include a single dose or dosage or multiple doses that are administered hourly, daily, weekly or monthly, or yearly. The amount or site of delivery is desirably selected based upon the identity and condition of the mammal.

The dosage unit of the vector suitable for delivery of the antigen to the mammal is described herein. The vector is prepared for administration by being suspended or dissolved in a pharmaceutically or physiologically acceptable carrier such as isotonic saline; isotonic salts solution or other formulations that will be apparent to those skilled in such administration. The appropriate carrier will be evident to those skilled in the art and will depend in large part upon the route of administration. The compositions of the invention may be administered to a mammal according to the routes described above, in a sustained release formulation using a biodegradable biocompatible polymer, or by on-site delivery using micelles, gels and liposomes. Optionally, the priming step of this invention also includes administering with the priming composition, a suitable amount of an adjuvant, such as are defined herein.

Preferably, a second composition is administered about 2 to about 27 weeks after administering the first, or preceding administration of an immunization composition, to the mammalian subject. The administration of the boosting composition is accomplished using an effective amount of a boosting composition containing a product that is the same, or cross-reactive, with that delivered via by the priming composition.

In another embodiment, the viral vectors of the invention are also well suited for use in a variety of other immunization and therapeutic regimens. Such uses will be readily apparent to one of skill in the art.

Dosages of the viral vector will depend primarily on factors such as the condition being treated, the age, weight and health of the patient, and may thus vary among mammalian (including human) patients. Advantageously, the unexpected potency of the recombinant simian (e.g., chimpanzee) adenoviruses of the invention permits the use significantly lower amount of the recombinant chimpanzee adenovirus to provide an effective amount to induce the desired immunogenic effect (e.g., induction of a predetermined level of antibodies and/or cytotoxic (CTL) immune response).

For example, for small animals, an effective dose of an adenoviral vector may be provided by $10^5$ particles/animal and $10^{11}$ particles/animal of adenovirus. For a larger animal, e.g., about 80 kg, $10^7$ to about $10^{13}$ particles per subject may be useful. However, higher doses may be readily selected, e.g., depending upon the selected route of delivery. For example, the adenoviral vector may be delivered in an amount which ranges from about 100 µL to about 100 ml, and more preferably, about 1 mL to about 10 mL, of carrier solution. The therapeutic levels, or levels of immunity, of the selected gene can be monitored to determine the need, if any, for boosters. Following an assessment of T cell response, or, antibody titers, in the serum, optional additional booster immunizations may be desired.

In one embodiment, an immunization regimen of the invention further involves administration of a DNA vaccine, e.g., via gene gun or plasmid. Such a DNA vaccine may be used as a priming step, which precedes a first adenoviral mediated delivery according to the invention. Alternatively, such a DNA vaccine may be used as a boost following one or more adenoviral administrations according to the invention.

In another embodiment, the regimen further involves sequential or co-administration of a protein-based vaccine. Such a vaccine can be used as a boost, following adenoviral-mediated delivery according to the invention. Alternatively, such a protein-based vaccine may be used as a prime, or in between one or more adenoviral-mediated immunizations in a regimen of the invention.

In one example, an immunization regimen of the invention provides a protective immune response to a disease-causing agent, e.g., a virus, bacteria or other organism, or a cross-reactive virus, bacteria or other disease-causing agent. In another example, the immunization regimen described herein can include a multiprotein regimen. See, e.g., R. R. Amara, *Science,* 292:69-74 (6 Apr. 2001) which describes a multiprotein regimen for expression of protein subunits useful for generating an immune response against HIV and SIV.

In another aspect, the invention provides a product useful for performing the immunization regimens described herein. Such a product can contain one or more of the adenoviral vectors described herein in a suitable container. Typically, such a product will further contain instructions for administration of the adenoviral vectors.

Further, the product may contain a physiologically acceptable carrier suitable for the selected route of delivery, e.g., for dilution and/or reconstitution of one or more the adenoviral vectors, syringes, vials, and the like.

The following examples are provided to illustrate the invention and do not limit the scope thereof. One skilled in the art will appreciate that although specific reagents and conditions are outlined in the following examples, modifications can be made that are meant to be encompassed by the spirit and scope of the invention.

Example 1

Ebola Zaire virus envelope glycoprotein (Ebo GP) was used as a model antigen to create a panel of C7 vaccine vectors, including C7.000CMVGP with a deletion in E1 region, C7.010CMVGP with deletions in both E1 and E3 regions, and C7.001CMVGP with deletions in both E1 and E4 regions. The transgene expression cassette was incorporated into E1 regions of these vectors.

A. Cell Lines

A549 cells were maintained in F-12K medium (Gibco-Life Technologies, Grand Island, N.Y.) supplemented with antibiotic and 10% FBS (Hyclone, Logan, Utah). 293T cells were maintained in DMEM (Gibco-Life Technologies) supplemented with antibiotic and 10% FBS (Hyclone).

B. Plasmids

Full-length cDNAs encoding the Ebola virus (species Zaire) VP40 or GP were cloned separately into a mammalian expression vector, pcDNA3.1 (Invitrogen, Carlsbad, Calif.), which contain the CMV promoter. The resulting plasmids were designated pcDNAEboZVP40 and pcDNAEboZGP.

C. Expression of EboZ GP from Transduced A549 Cells

A549 cells were transduced with recombinant adenoviral vectors (1,000 particles per cell or 10,000 particles per cell). Forty-eight hours later, cells were directly harvested into Laemmli sample buffer. After heating at 95° C. for 5 minutes, cell samples were centrifuged and supernatants were loaded onto SDS-polyacrylamide gel. After electrophoresis, proteins were transferred by electroblotting to a nitrocellulose membrane. The blot was visualized by ECL western blotting system (Amersham Pharmacia Biotech, Piscataway, N.J.), using a polyclonal antibody to EboZ GP as primary antibody at a dilution of 1:1,000 and horseradish peroxidase-conjugated goat anti-rabbit antibody (Santa Cruz Biotechnology, Santa Cruz, Calif.) as secondary antibody at a dilution of 1:5,000.

D. Production of EboZ Virus-Like-Particles (VLPs)

An endotoxin-free DNA mixture, containing 45 µg of pcDNAEboZVP40 and 45 µg of pcDNAEboZGP, was transfected into each 150 mm plate of 293T cells using CalPhos Mammalian Transfection Kit (BD Biosciences Clontech, Palo Alto, Calif.). Next day, cells were changed to fresh culture medium. Twenty-four hours later, medium were harvested and span three times at 2000 rpm for 5 minutes to remove cell debris. Cell-free supernatant containing VLPs was further concentrated by ultracentrifugation at 28,000 rpm through 20% sucrose cushion for 2 hours at 4° C. using a SW28 rotor (Beckman, Fullerton, Calif.). The concentrated VLPs were then resuspended into phosphate buffered saline (PBS) on ice for 5 hours and stored at −80° C. in small aliquots.

E. Creation of Molecular Clones of EboZ Expressing Adenovirus Vectors

Recombinant adenovirus genomes that derived from different species and strains of adenoviruses and express EboZGP were created through direct ligation and green/white selection system that was described elsewhere (Gao et al., *Gene Therapy*, 10(22):1926-1930 (October 2003) and Roy et al., *Human Gene Therapy*, 15(5):519-530 (May 2004). Briefly, the EboZGP cDNA was subcloned into a universal pShuttle plasmid vector between CMV promoter and bovine growth hormone poly A which was used for introducing the EboZGP into a variety of molecular clones of adenovirus backbones.

The molecular clones of adenovirus backbones include Human serotype 5 with E1 and E3 deletions (H5.040), Chimpanzee serotype 7 with E1 deletion only (C7.000), E1 and E3 deletions (C7.010) and E1 and E4 deletions (C7.001). The cloning process to create those molecular clones were described elsewhere (Gao et al., *Gene Therapy*, 10(22):1926-1930 (October 2003) and Roy et al., *Human Gene Therapy*, 15(5):519-530 (May 2004)). All these molecular clones containing a cassette that expressed prokaryotic GFP from bacterial lac promoter and flanked by two rare restriction sites, PI-Sce I and I-Ceu I. This allowed the EboZ expression cassette from the universal pShuttle construct to be swapped into the adenovirus molecular clones through a convenient and efficient green/white selection mediated cloning process (Gao et al., 2003, cited above).

1. Rescue, Expansion and Purification of AdEboZ Vectors

To rescue recombinant viruses from the molecular clones, the plasmid DNAs were linearized by appropriate restriction enzymes to release the vector genomes from plasmid backbones and transfected into appropriate cell lines. For E1/E4 deleted vectors, 10-3 cells, a 293 cell based E1/E4-complementing cell line with E4ORF6 expressed under Zinc induction were used. For all other constructs, 293 cells were used. Once full cytopathic effect (CPE), the sign of virus rescue and replication, was observed, crude viral lysate harvested for gradual expansion to large scale infections in appropriate cell lines. Viruses were purified by the standard CsCl gradient sedimentation method. The genome structures of recombinant viruses were confirmed by restriction enzyme analysis. For all vector except for E1/E4-deleted vectors, infectivity of the viruses were determined by plaque assay on 293 cells. However, the vectors used for immunization experiments were dosed based on virus physical particle numbers measured by OD260 readings on a UV-spectrophomometer.

By western blot analysis, C7.000CMVGP and C7.010CMVGP vectors yielded very similar level of GP expression, while C7.001CMVGP vector produced significantly less GP protein in transduced A549 cells.

Example 2

Priming of Mice with E4-Deleted Ad Vector Followed by Boost of E1-Deleted Ad Vector A. Mice B10BR mice (6-8 weeks old) were purchased from The Jackson Laboratory (Bar Harbor, Me.) and kept at the Animal Facility of The Wistar Institute (Philadelphia, Pa.). Mice were immunized with recombinant adenoviral vectors or recombinant adeno-associated viral vectors diluted in 100 µl PBS by intramuscular injection.

B. Peptide

The $H-2^K$ restricted EboZ GP-specific peptide (TELRTFSI peptide, SEQ ID NO:1) which carries the immunodominant MHC class I epitope of EboZ GP for mice of the $H-2^k$ haplotype was synthesized by Mimotopes (Victoria, Australia). Peptide was diluted in DMSO to a concentration of 5 mg/ml and stored at −80° C. Peptide was used at 2 µl and DMSO concentrations were kept below 0.1% (v/v) in all final assay mixtures.

C. Intracellular IFN-γ Staining

Splenocytes from immunized mice were stimulated with TELRTFSI peptide (SEQ ID NO:1) for 5 hours at 37° C. and 10% $CO_2$ in the presence of 1 µl Brefeldin A (GolgiPlug, BD PharMingen, San Diego, Calif.). Control cells were incubated without peptide. After washing, cells were stained with a FITC-labeled anti-mouse CD8 antibody (BD PharMingen). Then, cells will be washed and permeabilized in Cytofix/Cytoperm (BD PharMingen) for 20 minutes on ice. Subsequently, cells were washed again and stained with a PE-labeled anti-mouse IFN-γ antibody (BD PharMingen). After extensively washing, cells were examined by two-color flow cytometry and data were analyzed by WinMDI™ [Microsoft] cytometry data analysis software. Splenoctyes Overall, these data suggested that multi-defective adenoviral vectors are better vaccine carriers.

All publications cited in this specification are incorporated herein by reference. While the invention has been described with reference to particular embodiments, it will be appreciated that modifications can be made without departing from the spirit of the invention. Such modifications are intended to fall within the scope of the appended claims.

SEQUENCE LISTING

```
<160> NUMBER OF SEQ ID NOS: 1

<210> SEQ ID NO 1
<211> LENGTH: 8
<212> TYPE: PRT
<213> ORGANISM: Artificial
<220> FEATURE:
<223> OTHER INFORMATION: H-2k restricted eboZ GP-specific peptide

<400> SEQUENCE: 1

Thr Glu Leu Arg Thr Phe Ser Ile
1               5
``` incubated without the peptide to GP showed <0.5% IFN-gamma producing CD8+ T cells.

D. Measurement of Total IgG Response to EboZ GP by Enzyme-Linked Immunosorbent Assay (ELISA)

Mice were bled either by retro-orbital puncture at various times after immunization or by heart-puncture at the termination. Sera were prepared and tested for total IgG response to EboZ GP on 96-well plates coated with EboZ VLPs diluted in PBS. The plates were coated overnight at 4° C. and blocked for 2 hours with PBS containing 3% bovine serum albumin (BSA) at room temperature. After washing, sera diluted in PBS containing 1% BSA were added onto wells for 2 hours at room temperature. After washing, a 1:10,000 dilution of horseradish peroxidase-conjugated goat anti-mouse IgG (Sigma Chemicals, St. Louis, Mo.) was added to the wells for 1 hour at room temperature. After washing, TMB substrate (Sigma Chemicals) was added for 10-20 minutes and reaction was subsequently stopped by adding Stop Reagent (Sigma Chemicals). Optical density was red at 450 nm. A cut-off value for positive sample was calculated as the mean delta OD at 450 nm for naïve serum at a 1:100 dilution plus 3 times of standard deviations. The endpoint antibody titer of each sample tested was then defined as the reciprocal of the highest dilution of the serum with a delta OD at 450 nm, which was interpolated according to the linear regression analysis, above the cut-off value.

By intracellular cytokine staining with $H-2^k$ restricted GP-specific peptide as stimulant, similar frequencies of CD8+ T cells producing IFN-γ were observed in B10BR mice vaccinated with C7.000CMVGP or C7.001CMVGP, while slightly higher frequencies of CD8+ T cells producing IFN-γ were observed in B10BR mice vaccinated with C7.010CMVGP. Total IgG responses to GP, measured by ELISA, were equivalent in serum from vaccinated mice with either of these vectors.

Ongoing studies indicate that better GP-specific T cell and B cell responses can be achieved by priming with either C7.010CMVGP or C7.001CMVGP and boosting with H5CMVGP than by priming with C7.000CMVGP and boosting with H5CMVGP.

The invention claimed is:

1. A method of priming an immune response to a target expressed from a boosting adenovirus without priming an anti-adenovirus immune response to the subsequently administered boosting adenovirus, comprising:

(a) administering a priming dose of an E1-deleted, E4-deleted adenovirus having a capsid of a first serotype, the priming adenovirus comprising an adenovirus genome comprising sequences encoding the adenovirus E3 gene operably linked to expression control sequences which direct expression of the E3 gene product and a functional deletion in at least adenovirus early genes E1 and E4, said genome further comprising a heterologous expression cassette comprising a nucleic acid sequence encoding a product for inducing an immune response to a target under the control of regulatory control sequences which direct expression of the product, which expression cassette is located in the site of the E1 deletion or the E4-deletion, wherein the priming adenovirus confers reduced anti-adenovirus immune response to the subsequently administered boosting adenovirus; and (b) administering the boosting dose of an adenovirus which is an E1-deleted adenovirus having a capsid of a second serotype that differs from the first serotype, the boosting adenovirus further comprising an adenovirus genome comprising heterologous expression cassette comprising nucleic acid sequence encoding the product for inducing an immune response to the target or a cross-reactive target under the control of regulatory control sequences which direct expression of the product in the site of the E1 deletion, the genome further comprising a functional deletion in at least the E1 gene, wherein the boosting E1-deleted adenovirus is administered after said priming adenovirus, wherein the immune responses to the product of the boosting adenovirus are greater.

2. The method according to claim 1, wherein the regulatory sequences for the product are different in the adenovirus of (a) and (b).

3. The method according to claim 1, wherein the immune response is an antigen-specific antibody response.

4. The method according to claim 1, wherein the immune response is an antigen-specific CTL response.

5. The method according to claim 1, wherein the capsid of (a) or (b) is selected from the group consisting of C5, C7 and C9.

6. The method according to claim 1, wherein the E3 gene product is expressed under control of a heterologous promoter.

7. The method according to claim 1, wherein the first and second product are the same.

8. The method according to claim 1, wherein the first and second product induce immune responses which are cross-reactive.

9. The method according to claim 1, wherein the regulatory sequences in the heterologous expression cassettes of (a) and (b) are different.

10. A method of reducing the immune response to a boosting adenoviral vector, comprising:
   (a) constructing a priming E1-deleted, E4-deleted adenovirus which comprises an adenovirus E3 gene operably linked to sequences which direct expression thereof, a first heterologous expression cassette comprising a nucleic acid sequence encoding a first product that induces an immune response to a target under the control of regulatory control sequences which direct expression of the product, and which adenovirus genome further comprises at least an adenovirus early gene E1-deleted region and adenovirus early gene E4-deleted region, the priming adenovirus having a first capsid, wherein the adenovirus early gene deletions reduce the anti-adenovirus response to a boosting adenovirus; and
   (b) administering after the priming adenovirus of (a) an E1-deleted boosting adenovirus having a second capsid that is immunologically distinct from the first capsid, the boosting adenovirus comprising an adenovirus genome comprising an E1-deleted region, and further comprising a second heterologous expression cassette comprising nucleic acid sequence encoding a second product for inducing an immune response to the target or a cross-reactive target under the control of regulatory control sequences which direct expression of the product, wherein the immune response to the second product is primed by the priming adenovirus of (a) without priming of an immune response to the boosting adenovirus.

11. The method according to claim 10, wherein the priming adenovirus comprises an adenovirus early gene region which expresses the E3 gene product under control of a heterologous promoter.

* * * * *